United States Patent [19]
Johansen

[11] Patent Number: 5,234,341
[45] Date of Patent: Aug. 10, 1993

[54] WEARER-REMOVABLE DENTAL IMPLANT ATTACHMENT

[76] Inventor: Raymond J. Johansen, 2000 State St., Santa Barbara, Calif. 93105

[21] Appl. No.: 930,281

[22] Filed: Aug. 17, 1992

[51] Int. Cl.$^5$ .................... A61C 13/12; A61C 13/225
[52] U.S. Cl. .................................... 433/172; 433/173
[58] Field of Search ............. 433/172, 173, 191, 193, 433/195

[56] References Cited

U.S. PATENT DOCUMENTS

| | | | |
|---|---|---|---|
| 4,085,506 | 4/1978 | Lew | 433/172 |
| 4,406,622 | 9/1983 | Yoon | 433/172 |
| 4,544,358 | 10/1985 | Montero | 433/172 |
| 4,850,869 | 7/1989 | Steinfort et al. | 433/172 |
| 4,863,382 | 9/1989 | Bookstaber | 433/172 |
| 4,904,186 | 2/1990 | Mays | 433/172 |
| 5,106,299 | 4/1992 | Ghalili | 433/172 |

FOREIGN PATENT DOCUMENTS

| | | | |
|---|---|---|---|
| 1203551 | 1/1960 | France | 433/172 |
| 1340429 | 9/1963 | France | 433/172 |

Primary Examiner—Gene Mancene
Assistant Examiner—Nicholas D. Lucchesi
Attorney, Agent, or Firm—Robert M. Sperry

[57] ABSTRACT

An improved dental implant prosthesis attachment comprising an attachment having hollow receptacles embedded within the prosthesis and formed with openings for receiving the heads of the mounting posts, and slide members which are removably insertable into the receptacles, by the wearer, to fixedly retain the heads of the posts within the receptacles and which are removable by the wearer to permit cleaning of the prosthesis and subjacent gum area.

10 Claims, 3 Drawing Sheets

WEARER-REMOVABLE DENTAL IMPLANT ATTACHMENT

BACKGROUND

1. Field of Invention

This invention relates to dental implants and is particularly directed to improved dental implant attachments which enable the prosthesis to quickly and easily be removed and reinstalled by the wearer.

2. Prior Art

Dental implants have been available for several years now and, conventionally, have been installed by imbedding a fixture in the patient's jaw for osseointegration, threading several mounting posts into this fixture and securing a dental prosthesis to these mounting posts to provide a restoration which simulates natural teeth in most aesthetic and functional attributes. Thus, dental implant prostheses are fixedly mounted in the wearer's mouth and, hence, will not slip during usage, which is a common complaint of traditional dental prostheses. However, permanently mounted dental prostheses must be mounted so that there is adequate space between the prosthesis and the gumline to provide access for daily cleaning of the implants and attach components. Otherwise, plaque accumulation around the implants will cause bone loss, abscess and eventual loss of the implant. Unfortunately, providing this cleaning space causes problems for the patient including food impaction, poor phonics (air escaping under the prosthesis) and, most of all, unacceptable aesthetics. Moreover, permanently mounted dental implant prostheses must periodically be removed by a dentist for cleaning, inspection and the like, which causes considerable expense and inconvenience to the wearer. Alternatively, dental implant prostheses must be of the removable type, in which the implants are used to stabilize the prosthesis with ball and O-ring attachments or "bar and clip" type attachments. With the removable type prosthesis, an acrylic flange can be included to extend over and hide the implant components. With this arrangement, no cleaning space is necessary between the prosthesis and the gum because the wearer is able to remove the prosthesis to perform thorough cleaning of the implants and the subjacent gum area. Because the implant components are hidden, the removable dental prostheses are more aesthetically pleasing. However, the main disadvantage of the removable prostheses is its inherent lack of stability and the possibility of its becoming dislodged during use. Along with this comes lack of the patient's confidence in and acceptance of the prosthesis. Also, it has been found that the flexible O-rings and clips become fatigued with use and tend to loosen and to allow slippage and disattachment of the prosthesis from the mounting posts, causing problems similar to those encountered by wearers of conventional non-implant dental prostheses. A search in the United States Patent Office has revealed the following:

| U.S. Pat. No. | INVENTOR | ISSUED |
|---|---|---|
| 5,064,374 | D. Lundgren | Nov. 12, 1991 |
| 5,051,091 | P. J. Rosenfeld | Sep. 24, 1991 |
| 4,988,292 | D. B. Rosen | Jan. 29, 1991 |
| 4,931,016 | R. Sillard | Jun. 5, 1990 |

Each of these references is subject to the deficiencies noted above. Thus, none of the prior art dental implants have been entirely satisfactory.

BRIEF SUMMARY AND OBJECTS OF INVENTION

These disadvantages of the prior art are overcome with the present invention and an improved dental implant attachment is provided having a prosthesis which can quickly and easily be removed by the wearer and, thus, can have all the aesthetic advantages of the removable prosthesis, yet which is fixedly mounted to the posts and, hence, is not subject to slippage or inadvertent detachment of the prosthesis from the posts.

The advantages of the present invention are preferably attained by providing an attachment having hollow receptacles contained within the prosthesis formed with openings for receiving the heads of the mounting posts and having slide means, which are insertable into the receptacles, by the wearer, to fixedly retain the heads of the posts within the receptacles, and which are removable by the wearer to permit cleaning of the implants and subjacent gum area.

Accordingly, it is an object of the present invention to provide an improved dental implant attachment.

Another object of the present invention is to provide an improved dental implant attachment having means for hiding the posts to prevent the posts from being visible when the wearer opens their mouth.

A further object of the present invention is to provide an improved dental implant attachment allowing a prosthesis which is removable by the wearer, yet which is fixedly attachable to the mounting posts and is not subject to slippage or detachment.

An additional object of the present invention is to provide an improved dental implant attachment allowing a prosthesis which is fixedly attached to the mounting posts, yet which is removable by the wearer to permit cleaning of the prosthesis implants and the subjacent gum area.

A specific object of the present invention is to provide an improved dental implant attachment comprising an attachment having hollow receptacles contained within the prosthesis formed with openings for receiving the heads of the mounting posts and having slide means which are insertable into the receptacles, by the wearer, to fixedly retain the heads of the posts within the receptacles and which are removable by the wearer to permit cleaning of the plate and subjacent gum area.

These and other objects and features of the present invention will be apparent from the following detailed description, taken with reference to the figures of the accompanying drawing.

DETAILED DESCRIPTION OF THE INVENTION

Figure 1:
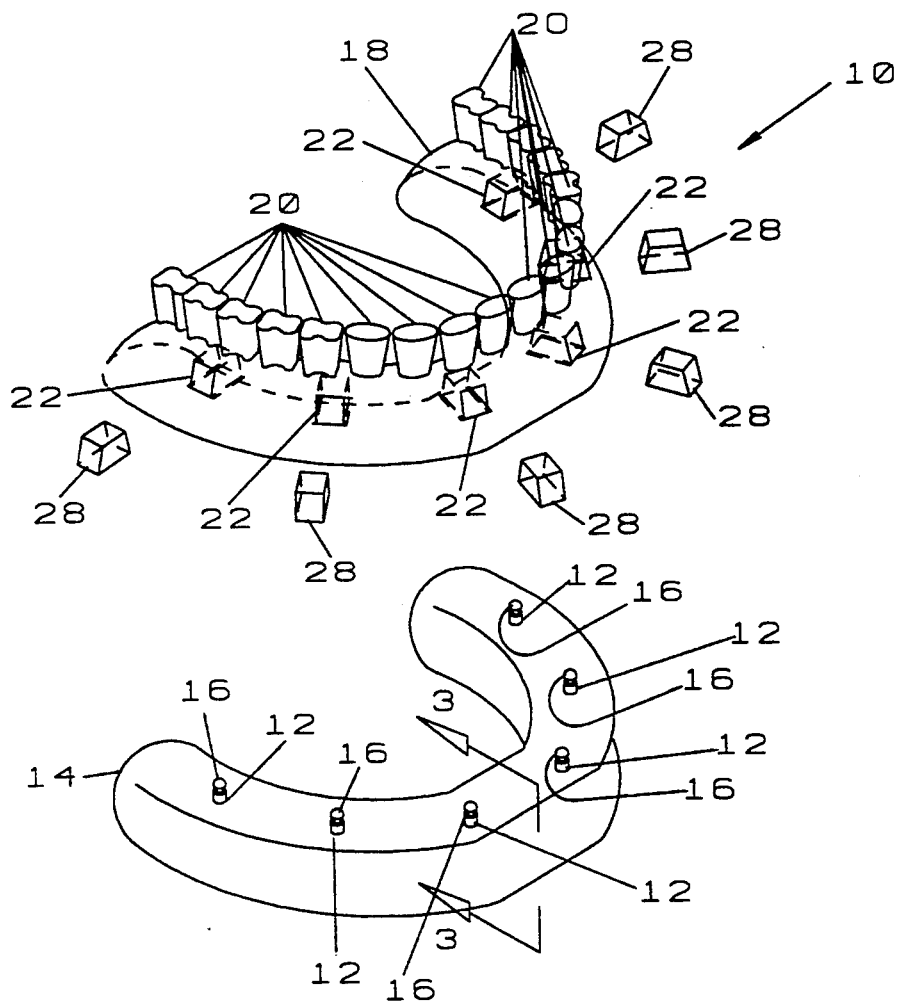
FIG. 1 is an exploded diagrammatic representation of a dental prosthesis embodying the present invention, together with a portion of a patient's jaw and the posts for mounting the prosthesis.
Figure 2:
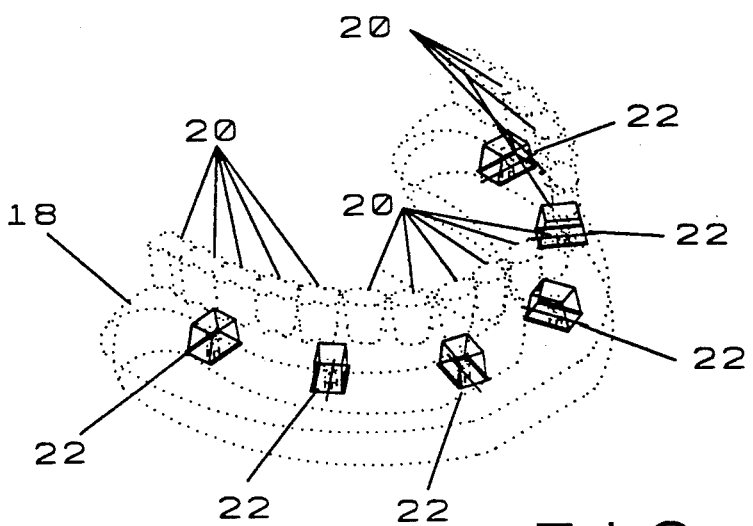
FIG. 2 is a diagrammatic representation of the prosthesis of FIG. 1 shown in phantom to permit illustration of the attaching receptacles.
Figure 3:
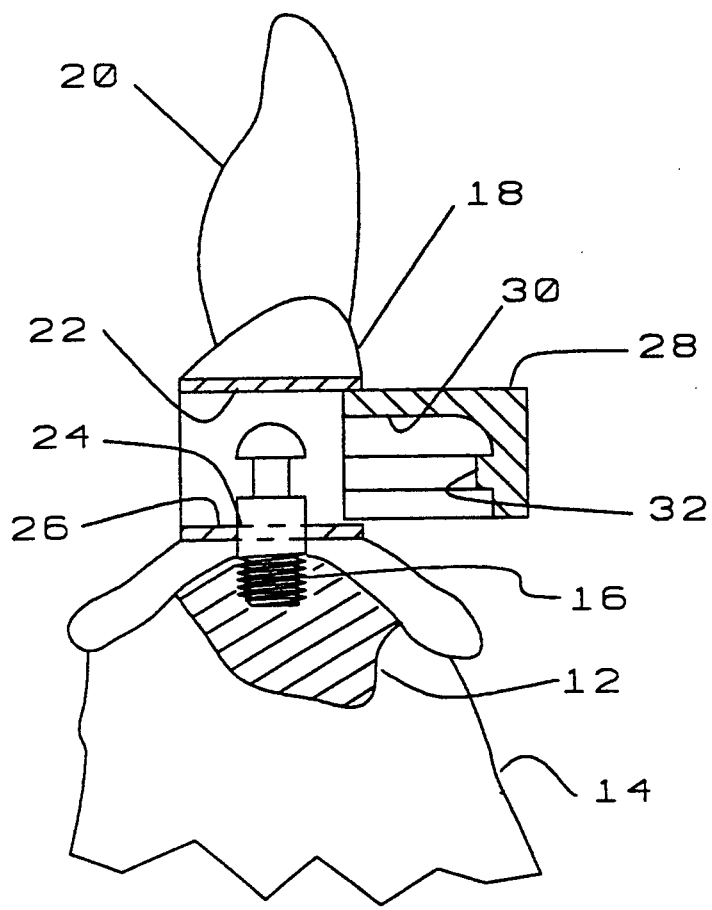
FIG. 3 is an enlarged sectional view through the dental prosthesis and attachment of FIG. 1, taken on the line 3—3 of FIG. 1, shown with the prosthesis mounted on the posts and with the slide means partially removed for clarity.
Figure 4:
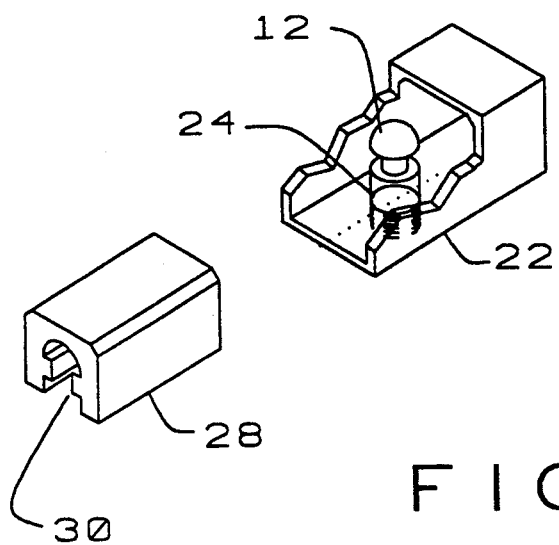
FIG. 4 is an exploded isometric view of the slide means and receptacle of the dental prosthesis of FIG. 1.

In that form of the present invention chosen for purposes of illustration in the drawing, FIG. 1 shows a dental prosthesis, indicated generally at 10, comprising a plurality of implants 12 embedded for osseointegration in the jaw 14 of a patient. A plurality of mounting posts 16 are provided, each threaded into a respective one of the implants 12. A dental prosthesis 18 carrying one or more false teeth 20 is provided and has an underside, not shown, formed to mate with the jaw 14, as with conventional dental prostheses, and has a plurality of recesses for receiving the mounting posts 16, as with conventional dental implant prostheses. However, in accordance with the present invention, the prosthesis 18 has one or more receptacles or tunnel members 22 embedded within the plastic or ceramic material of the prosthesis 18 and extending completely through the prosthesis 18, as best seen in FIGS. 2 and 3. As best seen in FIG. 3, the tunnel members 22 communicate with the exterior surface of the prosthesis 18, on both the inner and outer sides, and are provided with openings 24 in the bottom surfaces 26 of the tunnel 22 to permit entry of the mounting post 16 into the interior of the tunnel member 22. Finally, slide members 28 are provided which are frictionally slideable into each of the tunnel members 22. As best seen in FIGS. 3 and 4, the slide members 28 are each formed with a recess 30 which is configured to receive the mounting posts 16 and serve to releasably lock the tunnel members 22 and, hence, the prosthesis 18 to the mounting posts 16. As best seen in FIG. 3, the recess 30 extends only part way through the slide member 28. Thus, when the slide member 28 is fully seated, the inner end 32 of the recess 30 will bear against the mounting post 16 to assure proper positioning of the slide member 28 and to provide a tactile indication to the wearer that the slide member 28 is in the "locked" position. The tunnel members 22 may be formed of any suitable material, such as metal. The slide members 28 are preferably formed of somewhat resilient material, such as nylon, to provide a cushioning action. However, if desired, the slide members 28 may be made of any suitable material which will serve to releasably lock the prosthesis 18 to the mounting posts 16. At least two of the tunnel members 22 are required to assure balanced locking of the prosthesis 18 to the mounting posts 16. However, if desired, one tunnel member 22 may be provided for each of the mounting posts 16.

In use, the wearer places the prosthesis 18 in his mouth, with the mounting posts 16 projecting into the recesses, not shown, on the underside of prosthesis 18 and with at least two of the mounting posts 16 projecting through the openings 24 into the interiors of the tunnel members 22. Thereafter, the wearer inserts one of the slide members 28 into each of the tunnel members 22 and pushes the slide member 28 into the tunnel member 22 so that the inner end 32 of recess 30 of the slide member 28 engages the mounting post 16. This indicates to the wearer that the slide member 28 is in the "locked" position and that the prosthesis 18 is securely locked onto the mounting posts 16. To remove the prosthesis 18, the wearer inserts a toothpick or the like into the inner opening of the tunnel member 22 and simply pushes the slide member 28 out of the tunnel member 22. This releases the mounting posts 16 and allows the wearer to remove the prosthesis 18 to clean the prosthesis 18 and the gum area around the posts 16 and implants 14. It will be apparent that the wearer can insert and remove the slide members 28 quickly and easily to permit removal and anchoring of the prosthesis 18 whenever necessary or desirable. At the same time, when the slide members 28 are inserted into the tunnel members 22, the prosthesis 18 will be firmly and securely locked onto the mounting posts 16 with no looseness or danger of slippage or dislocation. Since only the outer ends of the tunnel members 22 will be visible when the wearer opens his mouth, the device of the present invention will be aesthetically pleasing and, if the slide members 28 are formed of nylon, the slide members 28 may be colored to match the material of the plate 18 to further minimize the visibility of the device of the present invention.

Figure 5:
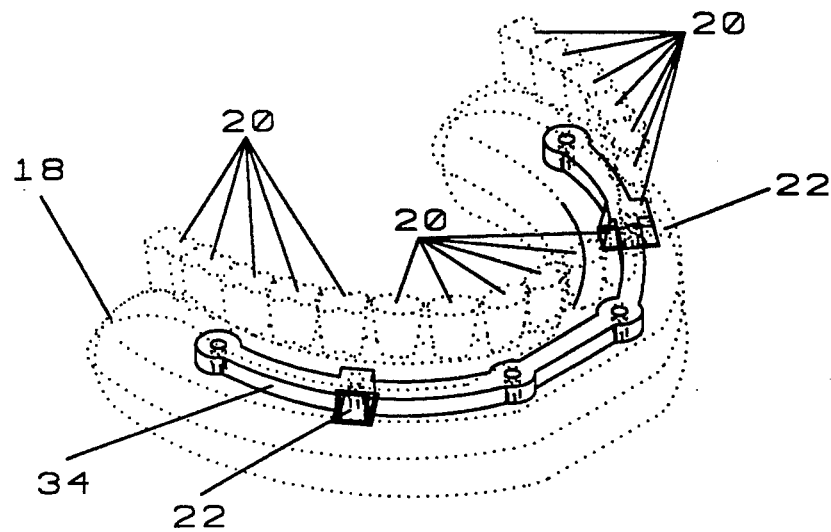
FIG. 5 is a view, similar to that of FIG. 2, showing an alternative form of support means for integrating the receptacles with the prosthesis of FIG. 1.

FIG. 5 shows an alternative means for mounting the tunnel members 22 to the prosthesis 18. As is well known, it is common to embed metal support frames, such as frame 34, within the plastic or ceramic material composing the dental prosthesis 18. When this is done, the tunnel members 22 may be formed integral with the frame 34, as shown in FIG. 5, and may be embedded into the prosthesis 18 with the frame 34. Of course, the tunnel members 22 must project from both sides of the frame 34 to ensure that the ends of the tunnel members 22 will communicate with the exterior of the prosthesis 18 to enable the slide members 28 to be inserted into and removed from the tunnel members 22.

Figure 6:
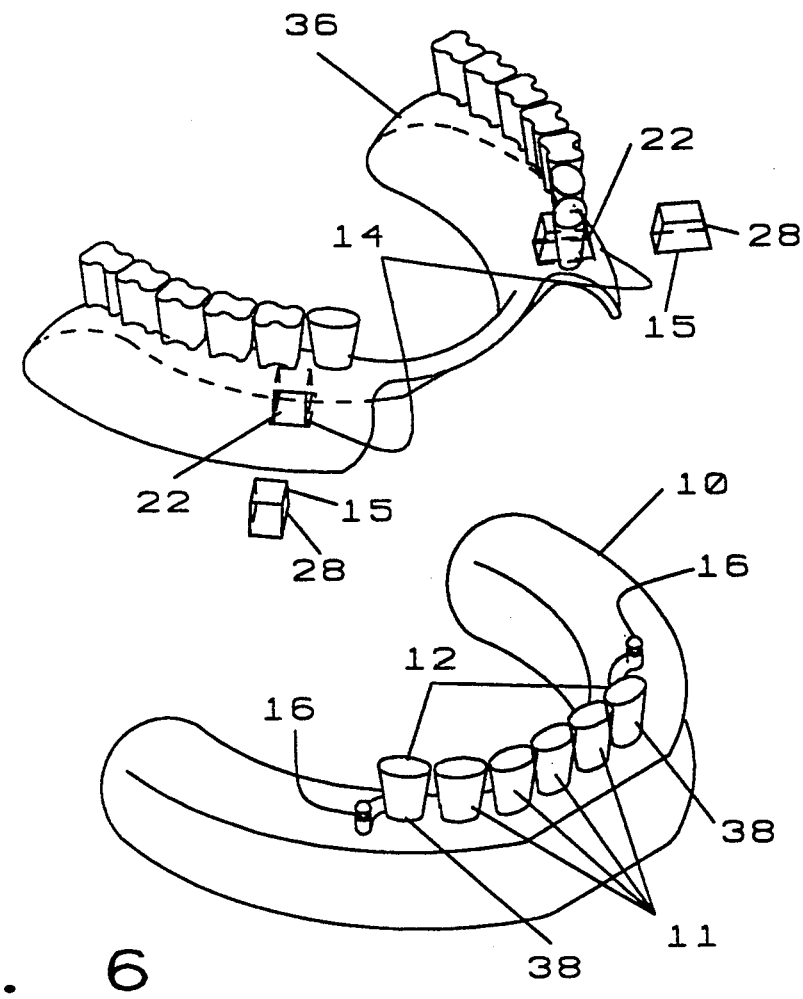
FIG. 6 is an exploded view showing a partial prosthesis embodying the present invention with the mounting posts secured to adjacent live teeth.

FIG. 6 shows a further alternative form of the present invention for use with a partial prosthesis, indicated generally at 36. As is well known, mounting posts 16 may be secured to live teeth, such as teeth 38, by full coverage crowns 40. As described above with respect to full prosthesis 18, tunnel members 22 may be embedded in the plastic or ceramic material of the partial prosthesis 36, in a manner such that the tunnel members 22 communicate with both the inner and outer surfaces of the prosthesis 36, and slide members 28 may be removeably inserted into the tunnel members 22 to releasably lock the tunnel members 22 and, hence, the prosthesis 36 to the posts 16.

Obviously, if desired, the dental implant of the present invention may also be incorporated into partial plates and made to releasably lock the partial plate to adjacent live teeth. In addition, numerous other variations and modifications may be made without departing from the spirit of the present invention. Therefore, it should be clearly understood that the forms of the present invention described above and shown in the accompanying drawings are illustrative only and are not intended to limit the scope of the present invention.

What is claimed is:

1. A dental implant prosthesis comprising:
   a plurality of mounting posts fixedly mounted within a wearer's mouth, each of said posts having a head portion,
   a dental prosthesis,
   a plurality of hollow receptacles embedded within said prosthesis and communicating with the inner and outer exterior surfaces of said prosthesis, said receptacles each formed with an opening for receiving a respective mounting post, and at least one slide means insertable into said receptacle to fixedly retain said posts within said receptacle and removable to allow said prosthesis to be taken out of the wearer's mouth leaving only said posts remaining in the wearer's mouth, each said slide means having a cavity for receiving a head portion of a respective post.

2. The device of claim 1 wherein:
said slide means are insertable and removable by the wearer at will.

3. The device of claim 1 wherein:
said receptacle are formed of metal.

4. The device of claim 1 wherein:
said slide means are formed of nylon.

5. The device of claim 1 wherein:
said slide means are colored to match the material of said prosthesis.

6. The device of claim 1 wherein:
said posts are mounted in implants embedded in the wearer's jaw for osseointegration with the wearer's jawbone.

7. The device of claim 1 wherein:
said posts are fixedly secured to adjacent ones of the wearer's live teeth, and
said prosthesis is a partial.

8. The device of claim 1 wherein:
said slide means are formed to releasably lock a mounting post within a receptacle.

9. The device of claim 1 wherein:
at least two of said receptacles are embedded in said prosthesis.

10. The device of claim 1 wherein:
said prosthesis is a full prosthesis.

* * * * *